(12) United States Patent
Stroppolo et al.

(10) Patent No.: US 10,016,359 B2
(45) Date of Patent: Jul. 10, 2018

(54) SOLID FORMS CONTAINING MELOXICAM WITH IMPROVED BUCCAL TASTE AND PROCESS FOR THEIR PREPARATION

(75) Inventors: Federico Stroppolo, Mezzovico (CH); Shahbaz Ardalan, Massagno (CH)

(73) Assignee: ALPEX PHARMA SA, Mezzovico (IT)

( * ) Notice: Subject to any disclaimer, the term of this patent is extended or adjusted under 35 U.S.C. 154(b) by 610 days.

(21) Appl. No.: 12/299,838

(22) PCT Filed: Jun. 11, 2007

(86) PCT No.: PCT/EP2007/055706
§ 371 (c)(1),
(2), (4) Date: Nov. 6, 2008

(87) PCT Pub. No.: WO2007/144323
PCT Pub. Date: Dec. 21, 2007

(65) Prior Publication Data
US 2009/0197874 A1     Aug. 6, 2009

(30) Foreign Application Priority Data
Jun. 15, 2006  (EP) ..................................... 06012353

(51) Int. Cl.
*A61K 31/415*     (2006.01)
*A61K 9/00*       (2006.01)
*A61K 9/20*       (2006.01)
*A61K 31/5415*    (2006.01)

(52) U.S. Cl.
CPC .......... *A61K 9/0056* (2013.01); *A61K 9/2013* (2013.01); *A61K 9/2018* (2013.01); *A61K 9/2027* (2013.01); *A61K 31/5415* (2013.01)

(58) Field of Classification Search
USPC ......................................................... 514/364
See application file for complete search history.

(56) References Cited

U.S. PATENT DOCUMENTS

| 6,184,220 B1 | 2/2001 | Tuerck et al. | |
| 2004/0234596 A1* | 11/2004 | Ohki et al. | ..................... 424/465 |
| 2005/0118258 A1 | 6/2005 | Shroppolo et al. | |
| 2005/0119239 A1* | 6/2005 | Wienrich et al. | ............. 514/165 |
| 2005/0187213 A1* | 8/2005 | Lang | .................. A61K 31/5415 |
| | | | 514/226.5 |

FOREIGN PATENT DOCUMENTS

| CN | 1546033 A1 | 11/2004 |
| WO | 99/09988 A | 3/1999 |
| WO | 2005/117895 A2 | 12/2005 |

* cited by examiner

*Primary Examiner* — Kathrien A Cruz
(74) *Attorney, Agent, or Firm* — Rothwell, Figg, Ernst & Manbeck, P.C.

(57) ABSTRACT

A solid dosage form of meloxicam containing an acid and sugars or polyalcohols or a mixture thereof.

3 Claims, No Drawings

SOLID FORMS CONTAINING MELOXICAM WITH IMPROVED BUCCAL TASTE AND PROCESS FOR THEIR PREPARATION

CROSS REFERENCE TO RELATED APPLICATION

This application is a 35 U.S.C. 371 National Phase Entry Application from PCT/EP2007/055706, filed Jun. 11, 2007, which claims the benefit of European Patent Application No. 06012353.6 filed on Jun. 15, 2006, the disclosure of which is incorporated herein in its entirety by reference.

The invention refers to solid forms containing meloxicam with improved buccal taste and to a method to improve taste of the non steroidal anti-inflammatory drug meloxicam starting from a solid dosage form for buccal administration.

The method consists in the use of a micronised form of meloxicam formulated in presence of an edible acid and a sugar or a polyalcohol.

BACKGROUND OF THE INVENTION

Swelling of solid dosage forms such as tablets (regular, film- or sugar-coated) and capsules (soft and hard), represent a problem causing difficult in ingestion for a significant portion of the adult population (about 30%). The incidence of these difficulties significantly increases in children and teenagers and in the elderly population in view of difficulty in ingestion.

Oral suspensions could solve the administration problem but present some drawbacks due to the weight of the container, usually consisting of glass and subsequent lack of comfort, e.g. when the patient travels.

For this reason, solid formulations which readily dissolve when administered are preferred.

Unfortunately not all active components can be formulated in oral disintegrating tablet (ODT) form, because of taste or stability problems.

In particular, when ODT dissolves into the oral cavity, the concentration of drug in the saliva is very high, due to the reduced volume of saliva (0.5-1.0 ml) causing taste problems.

Meloxicam, a known non steroidal anti-inflammatory drug (NSAID), is marketed by Boehringer-Ingelheim in the form of tablets, oral suspensions and suppositories.

Meloxicam, as most drugs belonging to the category of oxicams such as ampiroxicam, droxicam and piroxicam, is characterized by a bitter taste making difficult its buccal administration in form of oral disintegrating tablet.

CN1546033 (Chengu Shengnuo Sci. & Technology Dev. Co.) discloses ODT of meloxicam containing lactose, mannitol, crystalline cellulose, low substituted methyl-cellulose, propylene glycol ether, cross bonding polyvinylpyrrolidone, sodium hydrogen carbonate, citric acid, aspartame, perfume and magnesium stearate.

WO 2005/117895 (Boehringer Ingelheim) discloses solid dosage forms containing meloxicam in combination with another active ingredient in admixture with a pharmaceutically acceptable carrier.

WO 99/09988 (Hexal AG) discloses solid dosage forms of meloxicam with improved solubility and bioavailability.

DESCRIPTION OF THE INVENTION

Surprisingly, it has been found that by addition of an acid to a buccal formulation together with a mixture of polyalcohols, at least one of which having preferably a negative temperature of dissolution, the taste of the drug is greatly improved, allowing the oral administration of the drug in solid form, without any inconvenience for the patient.

The quantity of acid required in the formulation ranges from 0.1% to 900% by weight of meloxicam, preferably from 0.3% to 500% by weight of meloxicam and most preferably between 0.5% to 100% by weight of meloxicam. Particularly preferred amounts of acids range from 0.8% to 1.5% by weight of meloxicam.

The quantitative ratio of the polyalcohol mixture to meloxicam ranges from 1:1 to 1:100, most preferably from 1 to 10. The ratio between the polyalcohol having a negative temperature of dissolution versus the other polyalcohol(s) ranges from 0.1:50, preferably 0.5:50, most preferably 0.9:1.5.

The quantity of meloxicam is typically in the range of 0.5 to 30 mg per dose.

Examples of acids for use according to the invention include citric, tartaric, malic, gluconic acids, etc. Citric acid and tartaric acid are preferred.

Examples of sugar include glucose, fructose, lactose, maltose, idose, sucrose, mannose, gulose, talose, maltol, ribose, arabinose, xilose, lyxose, etc or mixture thereof.

Examples of polyalcohols include xylitol, mannitol, sorbitol, idole, etc.

Polyalcohols or sugars having a negative temperature of dissolution includes sorbitol, xylytol, maltol, maltitol, etc. These compounds when dissolved in water decrease the temperature of the generated solution.

The tablets of the invention could be obtained by a process including direct blending, wet granulation or fluid-bed granulation.

In case of fluid bed granulation the sieved powder of meloxicam, polyalcohols, acid, and other excipients such as sweetening agents, are granulated with a water solution containing a binder, such as polyvinylpyrrolidone, PEG, sodium carboxymethyl cellulose etc followed by drying, blending of the granular with lubricants (e.g. magnesium stearate) and final tabletting.

The invention is illustrated by the following examples.

Example 1—Preparation of an Oral Dispersible Tablet Containing 15 mg of Meloxicam Oral dispersible tablets containing 15 mg of meloxicam were prepared as follows:

Polyvinylpyrrolidone (Kollidon®) (10 g) were dissolved in purified water (about 30 g).

Meloxicam (37.5 g), mannitol (560 g), sorbitol (277.5 g), citric acid (37.5 g), aspartame (20.0 g) and Kollidon® (20 g) were sieved and loaded in a fluid bed granulator Strea 1.

The powder was granulated with the above aqueous solution of Kollidon®.

The granular was then dried until a moisture not higher than 0.5% and cooled to room temperature.

The granular was then blended until homogeneity in a cube mixer with of flavour (25 g) and of magnesium stearate (12.5 g).

The blended product was then compressed in round shaped tablets with a diameter of 12 mm, weighing 400 mg and containing 15 mg of meloxicam.

Example 2—Preparation of an Oral Dispersible Tablet Containing 7.5 mg of Meloxicam Oral dispersible tablets containing 7.5 mg of meloxicam were prepared as follows.

A granular was prepared as described in the example 1.

The blended product was compressed in round shaped tablets with a diameter of 9.0 mm, weighing 200 mg and containing 7.5 mg of meloxicam.

Comparative Example 3

Kollidon® (10 g) were dissolved in purified water (about 30 g).

Meloxicam (37.5 g), citric acid (875 g), aspartame (20.0 g) and Kollidon® (20 g) were sieved and loaded in a fluid bed granulator Strea 1;

The powder was granulated with the above aqueous solution of Kollidon®.

The granular was then dried until a moisture not higher than 0.5% and cooled to room temperature.

The granular was then blended until homogeneity in a cube mixer with flavour (25 g) and magnesium stearate (12.5 g).

The blended product was then compressed in round shaped tablets with a diameter of 12 mm, weighing 400 mg and containing 15 mg of meloxicam.

Comparative Example 4

Kollidon® (10 g) were dissolved in purified water (about 30 g).

Meloxicam (37.5 g), mannitol (585 g), sorbitol (290 g), aspartame (20.0 g) and Kollidon® (20 g) were sieved and loaded in a fluid bed granulator Strea 1.

The powder was granulated with the above aqueous solution of Kollidon®.

The granular was then dried until a moisture limit of not more than 0.5% and cooled to room temperature.

The granular was then blended until homogeneity in a cube mixer with flavour (25 g) and magnesium stearate (12.5 g).

The blended product was then compressed in round shaped tablets with a diameter of 12 mm, weighing 400 mg and containing 15 mg of meloxicam.

Example 5

The taste of tablets manufactured according the examples 1 to 4 has been evaluated by administering the tablets to a group of 28 volunteers. The taste evaluation is reported below:

TABLE 1

| Example # | Very unpleasant | Unpleasant | Acceptable | Good | Excellent | General Comment |
|---|---|---|---|---|---|---|
| 1 | — | — | 10 | 23 | 67 | Like a candy |
| 2 | — | — | 8 | 24 | 68 | Like a candy |
| 3 | 71 | 26 | 1 | — | — | Too acid Unacceptable |
| 4 | 68 | 30 | 2 | — | — | Bitter Unacceptable |

The invention claimed is:

1. A buccal tablet containing meloxicam, a taste-masking formulation consisting of at least 0.5% by weight of citric acid wherein the ratio of said citric acid to meloxicam is 1:1, a combination of sorbitol and mannitol, and at least one further excipient selected from sweetening agents, binders, or lubricants, wherein said taste-masking formulation is present in an amount effective for masking said meloxicam's bitter taste in said buccal tablet, comprising the sorbitol and mannitol combination and meloxicam in a 837.5:37.5 weight ratio of the combination of sorbitol and mannitol to meloxicam.

2. A buccal tablet containing meloxicam, a taste-masking formulation consisting of at least 0.5% by weight of citric acid wherein the ratio of said citric acid to meloxicam is 1:1, a combination of sorbitol and mannitol, and at least one further excipient selected from sweetening agents, binders, or lubricants, wherein said taste-masking formulation is present in an amount effective for masking said meloxicam's bitter taste in said buccal tablet, wherein said taste-masking formulation comprises mannitol in a 560:37.5 mannitol to meloxicam weight ratio and sorbitol in a 277.5:37.5 sorbitol to meloxicam weight ratio.

3. The buccal tablet of claim 2, further comprising aspartame in a 20:37.5 aspartame to meloxicam weight ratio.

* * * * *